United States Patent
Ishikawa et al.

(10) Patent No.: US 11,170,480 B2
(45) Date of Patent: Nov. 9, 2021

(54) IMAGE ENHANCEMENT USING VIRTUAL AVERAGING

(71) Applicant: University of Pittsburgh - Of the Commonwealth System of Higher Education, Pittsburgh, PA (US)

(72) Inventors: Hiroshi Ishikawa, Allison Park, PA (US); Chieh-Li Chen, Seattle, WA (US); Joel Steven Schuman, Pittsburgh, PA (US); Chaim-Gadi Wollstein, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 34 days.

(21) Appl. No.: 15/568,398

(22) PCT Filed: Apr. 28, 2016

(86) PCT No.: PCT/US2016/029704
§ 371 (c)(1),
(2) Date: Oct. 20, 2017

(87) PCT Pub. No.: WO2016/176410
PCT Pub. Date: Nov. 3, 2016

(65) Prior Publication Data
US 2018/0158182 A1 Jun. 7, 2018

Related U.S. Application Data

(60) Provisional application No. 62/154,454, filed on Apr. 29, 2015.

(51) Int. Cl.
*G06T 5/50* (2006.01)
*A61B 3/10* (2006.01)
(Continued)

(52) U.S. Cl.
CPC ............... *G06T 5/50* (2013.01); *A61B 3/102* (2013.01); *G06T 5/002* (2013.01); *G06T 5/20* (2013.01);
(Continued)

(58) Field of Classification Search
CPC .. G06T 5/50; G06T 5/002; G06T 5/20; G06T 2207/10101; G06T 2207/20216;
(Continued)

(56) References Cited

U.S. PATENT DOCUMENTS

2006/0285635 A1* 12/2006 Boppart ............... A61B 5/0066
378/22
2007/0009144 A1 1/2007 Tsunashima et al.
(Continued)

FOREIGN PATENT DOCUMENTS

JP 2012-176291 A 9/2012

OTHER PUBLICATIONS

International Search Report and Written Opinion issued in related International Patent Application No. PCT/US2016/029704, completed Jul. 26, 2016.
(Continued)

*Primary Examiner* — Jianxun Yang
(74) *Attorney, Agent, or Firm* — Foley & Lardner LLP (57) ABSTRACT

The present invention is directed to systems and methods for generating virtually averaged optical coherence tomography (Oct.) images. An illustrative method can include receiving an image, identifying a first voxel of the image, and selecting a plurality of local voxels of the image. Each of the plurality of local voxels is within a defined region of the first voxel. The values of the plurality of local voxels can indicate an appearance of the local voxels in the image.

20 Claims, 3 Drawing Sheets

(51) Int. Cl.
*G06T 5/00* (2006.01)
*G06T 5/20* (2006.01)

(52) U.S. Cl.
CPC ............ *G06T 2207/10101* (2013.01); *G06T 2207/20216* (2013.01); *G06T 2207/30041* (2013.01)

(58) Field of Classification Search
CPC .......... G06T 2207/30041; A61B 3/102; A61B 5/0066; A61B 3/0025; A61B 5/0073; A61B 5/7203; A61B 5/7257; G01N 21/4795; G01N 2021/1787
See application file for complete search history.

(56) References Cited

U.S. PATENT DOCUMENTS

| | | | | |
|---|---|---|---|---|
| 2007/0197932 | A1* | 8/2007 | Feke | A61B 3/0025 600/558 |
| 2008/0212838 | A1* | 9/2008 | Frigerio | G06K 9/209 382/107 |
| 2011/0103658 | A1* | 5/2011 | Davis | G01N 21/4795 382/128 |
| 2013/0022287 | A1* | 1/2013 | Hooper | G06T 5/20 382/254 |
| 2013/0329012 | A1* | 12/2013 | Bartos | G01B 21/042 348/46 |
| 2014/1115141 | | 4/2014 | Takama | |
| 2014/0254907 | A1* | 9/2014 | Wang | G06T 7/143 382/131 |
| 2015/0015845 | A1 | 1/2015 | Spaide et al. | |

OTHER PUBLICATIONS

International Preliminary Report on Patentability issued in related Internationa Patent Application No. PCT/US2016/029704, dated Nov. 9, 2017.

* cited by examiner

IMAGE ENHANCEMENT USING VIRTUAL AVERAGING

CROSS-REFERENCE TO RELATED APPLICATIONS

This application is a U.S. National Stage under 35 U.S.C. § 371 of International Application No PCT/US2016/029704, titled "IMAGE ENHANCEMENT USING VIRTUAL AVERAGING," filed on Apr. 28, 2016, which claims priority to U.S. Provisional Patent Application No. 62/154,454 filed Apr. 29, 2015. The contents of the foregoing applictions are incorporated herein by reference in their entirety.

GOVERNMENT FUNDING

This invention was made with government support under grant numbers EY013178 and EY008098 awarded by the National Institutes of Health (NIH). The government has certain rights in the invention.

FIELD OF THE DISCLOSURE

This disclosure generally relates to systems and methods for improving optical coherence tomography images using virtual averaging.

BACKGROUND

Optical coherence tomography (OCT) is an ocular imaging technique used in clinical ophthalmological care. OCT uses a broad-bandwidth light source to generate cross-sectional, sub-surface images of the eye. There are many commercially available OCT devices. The different OCT devices provide a wide variety of options in terms of cost, scan protocols, image processing, and presentation. However, some OCT devices can cause discomfort to patients and it can be difficult or painful to obtain useful images of a patient's eye.

There is a need in the art for methods of improving the appearance and quality of OCT images. The present invention satisfies this need.

SUMMARY

An illustrative method for virtual averaging of optical coherence tomography (OCT) images can include (a) receiving an image, (b) identifying a first voxel of the image, and (c) selecting a plurality of local voxels of the image. Each of the plurality of local voxels is within a defined region of the first voxel. A plurality of modified voxel values of the image is then determined. In one embodiment of the invention, determining the plurality of modified voxel values is based on values of the plurality of local voxels. A virtually averaged voxel value is then determined by averaging the plurality of modified voxel values. The values of the plurality of local voxels can indicate an appearance of the local voxels in the image. Selecting the plurality of local voxels within the defined region of the first voxel, determining the plurality of modified voxels, and determining the virtually averaged voxel value can be repeated any number of times as required. For example, each process can be repeated multiple times, such as 2 or more, e.g., 15 times, for each identified first voxel. In one embodiment, the plurality of local voxels are in a two dimensional plane.

The method can also include determining a plurality of modified voxel values by adding a deviation to a value of each of the plurality of local voxels and determining a virtually averaged voxel value by averaging the plurality of modified voxel values. The deviation added to the value of each of the plurality of local voxels can be chosen using a Gaussian distribution. For example, selecting the selected portion of the plurality of local voxels can be based on a first random Gaussian distribution, and selecting a deviation value for each of the values of the selected portion of the plurality of local voxels can be based on a second random Gaussian distribution.

The OCT image used in the first step of the method can be an OCT image in which frame averaging was not used or an OCT image in which frame averaging was used. In addition, the image can comprise a plurality of voxels comprising values indicating an appearance of the image, wherein the plurality of voxels comprises the first voxel and the plurality of local voxels. Further, the plurality of voxels can comprise two or three dimensions.

In yet another embodiment, the method of the invention can further comprise identifying a next voxel of the image; selecting a second plurality of local voxels of the image, wherein each voxel of the second plurality of local voxels is within a defined region of the next voxel; determining a second plurality of modified voxel values of the image; and determining a second virtually averaged voxel value by averaging the second plurality of modified voxel values.

In one embodiment, the virtually averaged image, when compared to an original OCT image used in the method, has a more distinctive visible nasal side retinal nerve fiber layer.

An illustrative system for virtually averaging optical coherence tomography (OCT) images comprises one or more data processors and one or more storage devices storing instructions that, when executed by the one or more data processors, cause the one or more data processors to perform a method. The method can include (a) receiving an image, (b) identifying a first voxel of the image, and (c) selecting a plurality of local voxels of the image. Each of the plurality of local voxels is within a defined region of the first voxel. A plurality of modified voxel values of the image is then determined. This step can be based upon values of the plurality of local voxels. Finally, a virtually averaged voxel value is determined by averaging the plurality of voxel values, thereby producing a virtually averaged image. The values of the plurality of local voxels can indicate an appearance of the local voxels in the image. Selecting the plurality of local voxels within the defined region of the first voxel, determining the plurality of modified voxels, and determining the virtually averaged voxel value can be repeated any number of times as required. For example, each process can be repeated multiple times, such as 2 or more, e.g., 15 times, for each identified first voxel.

In one embodiment of the invention, the instructions can further cause the one or more data processors to determine the plurality of modified voxel values by adding a deviation value to values of a selected portion of the plurality of local voxels. For example, the instructions can further cause the one or more data processors to select the selected portion of the plurality of local voxels based on a first random Gaussian distribution. In addition, the instructions can further cause the one or more data processors to select a deviation value for each of the values of the selected portion of the plurality of local voxels based on a second random Gaussian distribution.

In another embodiment, the OCT image used in the first step of the method or system is an OCT image in which frame averaging was not used, or an OCT image in which frame averaging was used.

In one embodiment, the virtually averaged image, when compared to an original OCT image used in the method, has a more distinctive visible nasal side retinal nerve fiber layer.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part of the application. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and as illustrated in the figures, can be arranged, substituted, combined, and designed in a wide variety of different configurations, all of which are explicitly contemplated and made part of this disclosure.

A. OCT Devices and Current Methodologies Regarding Frame Averaging

Optical coherence tomography (OCT) devices are used regularly for clinical care in ophthalmology in part because such devices can generate high-resolution cross-sectional images of a patient's eye. The images can be obtained by OCT devices without contacting the eye and can be non-invasive. Such devices can also help provide objective assessments of the tissue structures of the eye.

In some instances, the accuracy of analysis of OCT images can suffer from the OCT image quality and appearance. Using lower quality OCT images can result in less confidence in acceptable segmentation results obtained using segmentation software. With the input of OCT images, segmentation software can populate a spreadsheet for user analytics and generate a report with statistical results and layer-wise thickness maps. This data can then be used by a clinician or physician to recommend treatment. Thus, lower quality OCT images used as a basis for segmentation software can impact resultant clinical analysis. Moreover, lower quality OCT images can also be difficult for physicians or others to observe morphological or other changes of the eye tissue. Accordingly, lower quality OCT images can cause clinical decisions to be more difficult or incorrect than if higher quality OCT images are used.

OCT devices obtain images of the eye by optically scanning across a patient's eye (e.g., retina). The OCT device obtains several data points while it makes a single pass across the patient's eye. To obtain three-dimensional images, the OCT device can make several passes across the patient's eye. However, making a pass across the eye is not instantaneous, but rather takes a period of time. To obtain the highest quality OCT image, the patient's eye must remain in the same position during the entire scan in relation to the OCT device's sensor. Some OCT devices are configured with an eye tracking system that can move the OCT device's sensor to follow the movement of the patient's eye. However, such eye tracking systems are not perfect. That is, even with eye tracking systems, the time to obtain an acceptable image of a cross-section of the patient's eye takes longer if the patient moves his or her eye than if the patient does not move his or her eye.

One method to compensate for discrepancies in the OCT image caused by a patient moving his or her eye is to backtrack in the scanning process and recapture a portion of the image of the eye. The more that the patient's eye moves, the more that the OCT device must scan. The overlapping portions of the captured image of the eye are averaged together. Such a technique is "frame averaging" or "signal averaging." The use of frame averaging generally improves the quality of the OCT image obtained by the OCT device.

While frame averaging can produce improved OCT images, the re-imaging of portions of the eye takes additional time to scan the patient's eye. Even with eye tracking systems, fast eye movement and blinking during a scan can result in the OCT device losing track of its place and having to start the scan again at the same location until there is no detectable motion or blinking for a scan. The longer a scan takes, the more likely that a patient is to make fast eye movements or blink and, therefore, prolong the time it takes the OCT device to obtain acceptable images. Further, many patients who require that their eye be scanned have issues with their eyes, and, therefore, it can be especially difficult or painful for the patient to maintain their eye in a stationary position for a period of time sufficient for the OCT device to complete a scan.

Accordingly, while frame averaging can produce improved OCT images, in some cases patients have a difficult or painful time completing a full OCT eye scan using frame averaging, if the patient can finish the scan at all, because of the extra time it takes for the frame averaging process. Additionally, not all OCT devices have eye-tracking systems or frame averaging capabilities. Furthermore, OCT images captured using different techniques (e.g., frame averaging, eye-tracking, etc.) can produce OCT images with variability between the images which can make comparison between OCT images captured using different techniques difficult. Some embodiments of the present disclosure can replicate the quality of OCT images that were obtained using frame averaging in OCT images in which frame averaging was not used.

As discussed, one scan across an eye can have multiple points. Deviations between points can be caused by slight relocation of the camera in relation to the eye, differences in corneal dryness (e.g., before and after blinking), slight incident angle differences caused by body motion, and other factors. In some embodiments, such deviations can follow a Gaussian distribution.

Some embodiments of the present disclosure can be used to shorten the scan time of OCT devices. As described in greater detail below, a method of virtually averaging OCT images can be used to improve the quality of OCT images that were obtained using a non-frame averaging method. In many instances, particularly for patients with a diseased eye, a scan of the patient's eye using frame averaging can take longer than the patient can bear. Thus, some embodiments of the present disclosure can allow an OCT device with frame averaging capabilities to capture an OCT image without using frame averaging (thereby reducing the scan time), where the OCT image can have a quality that is comparable to an OCT image captured with frame averaging. That is, embodiments of the present disclosure can shorten the scan time of a patient's eye without sacrificing quality.

B. Exemplary Structures of the Present Invention

Figure 1:
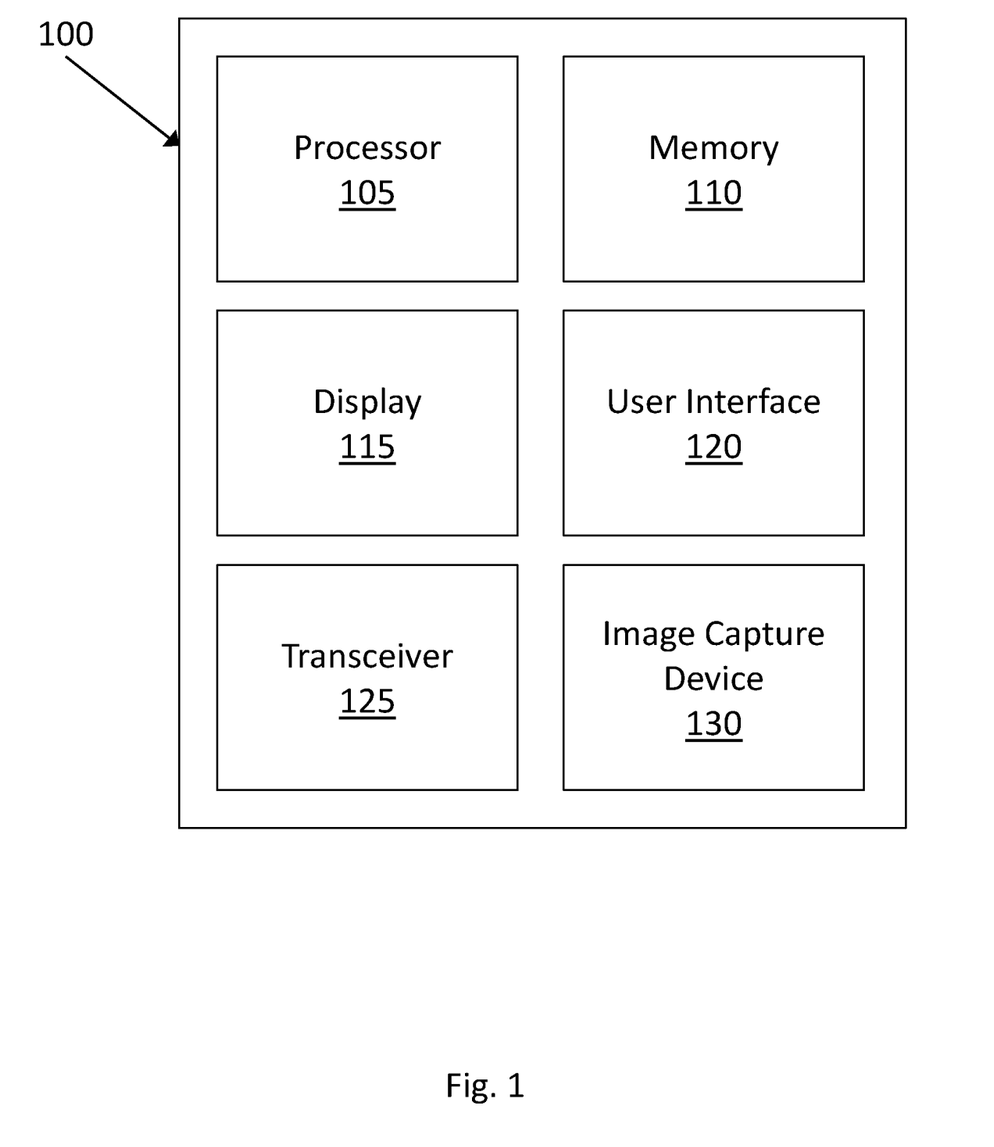
FIG. 1 is a block diagram of an image enhancement device in accordance with an illustrative embodiment.

FIG. 1 is a block diagram of an image enhancement device 100 in accordance with an illustrative embodiment. In alternative embodiments, additional, fewer, or different elements can be used. An illustrative image enhancement device 100 can include a processor 105, memory 110, display 115, user interface 120, a transceiver 125, and image capture device 130.

In some embodiments, the image enhancement device 100 can include a processor 105. The processor 105 can be configured to carry out and/or cause to be carried out one or more operations described herein. For example, the processor 105 can execute instructions as known to those skilled in the art. The instructions may be carried out by one or more special purpose computers, logic circuits, and/or hardware circuits. Thus, the processor 105 may be implemented in hardware, firmware, software, or any combination of these methods. The term "execution" is the process of running an application or the carrying out of the operation called for by an instruction. The instructions may be written using one or more programming languages, scripting language, assembly language, etc.

The processor 105 executes an instruction, meaning that it performs the operations called for by that instruction. The processor 105 operably couples with memory 110, transceiver 125, image capture device 130, user interface 120, etc. to receive, to send, and to process information and to control the operations of the image enhancement device 100. The processor 105 may retrieve a set of instructions from a permanent memory device such as a read-only memory (ROM) device and copy the instructions in an executable form to a temporary memory device that is generally some form of random access memory (RAM). The image enhancement device 100 may include a plurality of processors that use the same or a different processing technology. In an illustrative embodiment, the instructions may be stored in memory 110.

In some embodiments, the image enhancement device 100 can include memory 110. Memory 110 can be an electronic holding place or storage for information so that the information can be accessed by processor 105 as known to those skilled in the art. Memory 110 can include, but is not limited to, any type of random access memory (RAM), any type of read-only memory (ROM), any type of flash memory, etc. such as magnetic storage devices (e.g., hard disk, floppy disk, magnetic strips, etc.), optical disks (e.g., compact disk (CD), digital versatile disk (DVD), etc.), smart cards, flash memory devices, etc. The image enhancement device 100 may have one or more computer-readable media that use the same or a different memory media technology.

Additionally, the image enhancement device 100 may have one or more drives that support the loading of a memory medium such as a CD, a DVD, a flash memory card, etc. In some embodiments, memory 110 can be used to store images. Accordingly, in some embodiments, memory 110 can be used instead of image capture device 130 to provide images to image enhancement device 100.

In some embodiments, the image enhancement device 100 can include a transceiver 125. A transceiver 125 can be configured to receive and/or transmit information. In some embodiments, a transceiver 125 can communicate information via a wired connection, such as an Ethernet connection, one or more twisted pair wires, coaxial cables, fiber optic cables, etc. In some embodiments, a transceiver 125 can communicate information via a wireless connection using microwaves, infrared waves, radio waves, spread spectrum technologies, satellites, etc. A transceiver 125 can be configured to communicate with another device using cellular networks, local area networks, wide area networks, the Internet, etc. In some embodiments, one or more of the elements of an image enhancement device 100 communicate via wired or wireless communications.

In some embodiments, an image enhancement device 100 can include an image capture device 130. In other embodiments, an image capture device 130 can be an independent device and not integrated into the image enhancement device 100. An image capture device 130 can be configured to capture images of a retina. In some embodiments, an image capture device 130 can capture two-dimensional images. In other embodiments, an image capture device 130 can capture three-dimensional images. An image capture device 130 can be a still-image camera, a video camera, etc. An image capture device 130 can be configured, for example, to capture color images, black-and-white images, filtered images (e.g., a sepia filter, a color filter, a blurring filter, etc.), or images captured through one or more lenses (e.g., a magnification lens, a wide angle lens, etc.), etc. In some embodiments, an image capture device 130 (and/or processor 105) can modify one or more image settings or features, such as color, contrast, brightness, white scale, saturation, sharpness, etc. In an illustrative embodiment, an image capture device 130 can be an OCT device.

In some embodiments, an image enhancement device 100 can include a user interface 120. A user interface 120 can be configured to receive and/or provide information from/to a user. A user interface 120 can be any user interface known in the art. A user interface 120 can be an interface for receiving user input and/or machine instructions for entry into an image enhancement device 100 as known to those skilled in the art. A user interface 120 may use various input technologies including, but not limited to, a keyboard, a stylus and/or touch screen, a mouse, a track ball, a keypad, a microphone, voice recognition, motion recognition, disk drives, remote controllers, input ports, one or more buttons, dials, joysticks, etc. to allow an external source, such as a user, to enter information into the image enhancement device 100. A user interface 120 can be used to navigate menus, adjust options, adjust settings, adjust display, etc.

In some embodiments, an image enhancement device 100 can include a display 115. A display 115 can be configured to provide an interface for presenting information from an image enhancement device 100 to external systems, users, or memory. For example, a user interface 120 can include an interface for a display, a printer, a speaker, alarm/indicator lights, a network interface, a disk drive, a computer memory device, etc. A user interface 120 can include, for example, a color display, a cathode-ray tube (CRT), a liquid crystal display (LCD), a plasma display, an organic light-emitting diode (OLED) display, etc.

C. Methods According to the Invention

Figure 2:
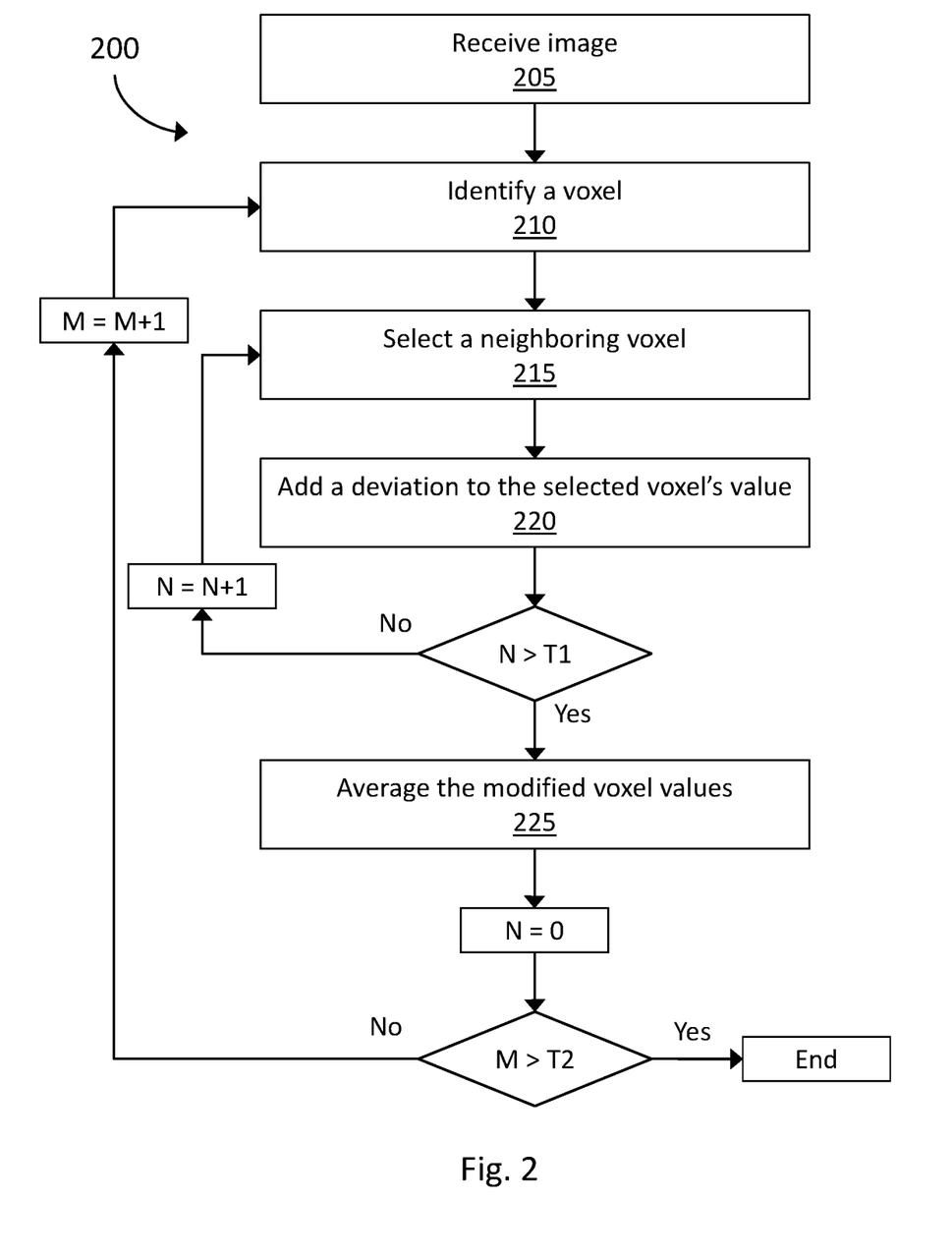
FIG. 2 shows a flow diagram of a method for enhancing images in accordance with an illustrative embodiment.
Figure 3:
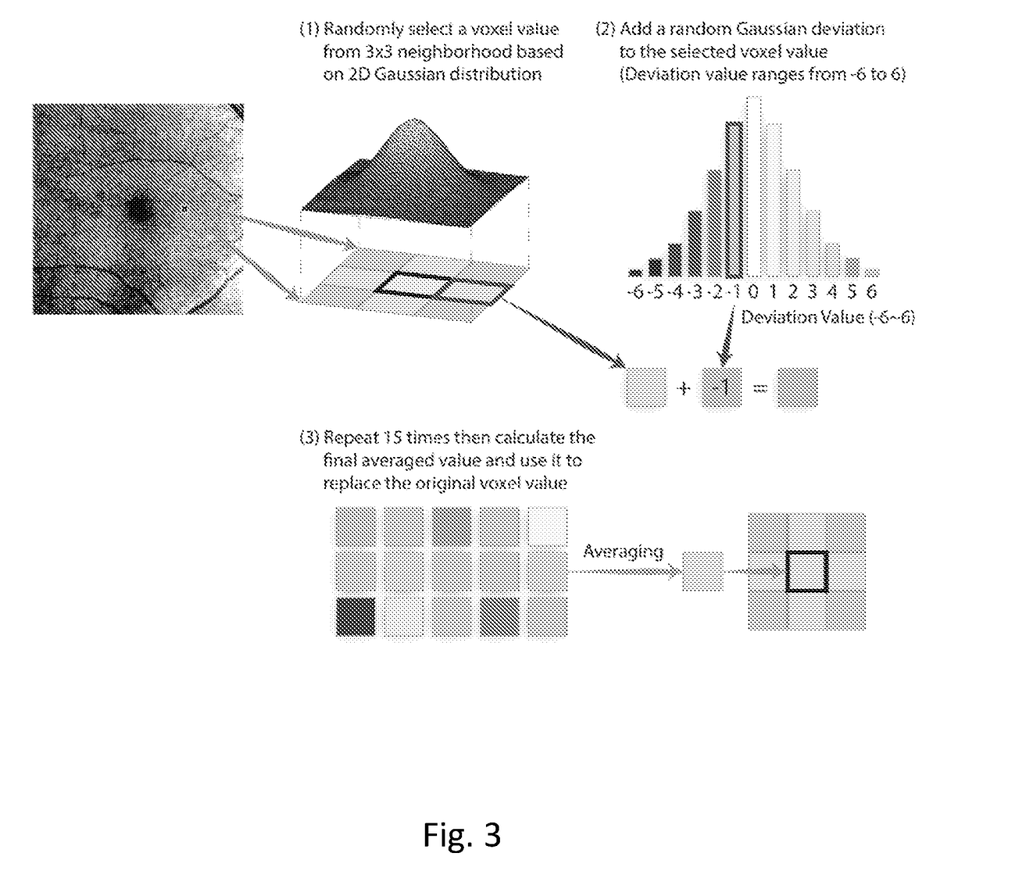
FIG. 3 illustrates an example of a method for enhancing images in accordance with an illustrative embodiment.

FIG. 2 shows a flow diagram of a method 200 for enhancing images in accordance with an illustrative embodiment. In alternative embodiments, fewer, additional, and/or different operations may be performed. Also, the use of a flow diagram is not meant to be limiting with respect to the order of operations performed. FIG. 3 illustrates an example of the method 200 for enhancing images in accordance with an illustrative embodiment. In alternative embodiments, fewer, additional, and/or different operations may be performed. Also, FIG. 3 is meant to be illustrative only, and not limiting.

In an operation 205, an image can be received. In some embodiments, the image can be an OCT image of an eye. In an illustrative embodiment, the image can be received from an OCT device. In another embodiment, the image can be received via a communications network, a memory storage device (e.g., a flash storage device), etc. The OCT image can be an OCT image that has not been frame averaged or it can be an image that has been frame averaged.

In an illustrative embodiment, software such as Cirrus HD-OCT can be used to collect OCT image data. In other embodiments, Specralis brand software can be used to collect OCT image data. In such embodiments, an OCT device capable of capturing frame averaged OCT images can be used to capture non-frame averaged OCT images. Macula Cube 200×200 and Optic Disc 200×200 protocols can be used to obtain the image data. In alternative embodiments, other suitable software and/or hardware known in the art can be used. For example, the methods and procedures described herein have been verified experimentally to work with commercial products such as the RTVue™ Real-Time Active Eye-Tracking OCT by Optovue, Bioptigen OCT by Leica Microsystems. The methods and procedures described herein have also been verified experimentally to work with prototype OCT units such as the Multi-modal AO OCT by Physical Sciences Inc. (PSI) and the Swept Source OCT developed by the Massachusetts Institute of Technology (MIT).

Any suitable size sampling grid can be used, any suitable number of samplings can be used, and any suitable scan depth can be used. For example, the images can be gathered by sampling a 200×200 voxel grid over a 6 millimeter (mm)×6 mm area of an eye centered on the foveola and/or the optic nerve head. The image can be captured with 1024 samplings within a 2.0 mm axial scan depth. In alternative embodiments, different settings or capture metrics can be used.

In some embodiments, multiple scans of the eye can be used such that the OCT images have good signal quality and spatial integrity. For example, OCT images with an image quality above the OCT device's manufacturer's recommended cutoff, OCT images with retina structures inside the scanning window and with no part of the retina cut off, and/or OCT images with little to no apparent eye movement during scanning can be considered to have good signal quality and/or spatial integrity. In some embodiments, OCT images with a signal strength greater than or equal to six can be considered to have good signal quality and/or spatial integrity. In such an embodiment, the signal strength range can be zero to ten with zero indicating no signal and ten indicating a strong signal. In other embodiments, a signal strength greater than or equal to 60% can be considered to have a good signal quality and/or spatial integrity. The signal strength can be computed by an OCT device. In other embodiments, a threshold greater than or less than six may be used. In such embodiments, the threshold used can be based on the method of determining signal strength. OCT images with little to no apparent eye movement can be OCT images in which there is no horizontal frame shift larger than one average size retinal blood vessel in diameter or a major distortion of the fovea or optic never head region. In some embodiments, OCT image quality can be determined by a computer or software. In other embodiments, a clinician can determine OCT image quality. In yet other embodiments, any combination of a clinician, a computer, and software can be used to determine OCT image quality.

In some embodiments, an operation 205 can include receiving raw image data and/or z-motion corrected raw data. Such raw data can be received from an OCT device. In other embodiments, an operation 205 can include receiving an image using a red, green, and blue color model, a YCbCr color space, a black and white color model, a grey scale model, etc. In some embodiments, images other than an OCT image of an eye can be used. In such embodiments, any digital image can be used. FIG. 3 shows one example of an OCT image that can be received.

In an operation 210, a voxel of the image is identified. In some embodiments, the received image can be comprised of a plurality of voxels. The plurality of voxels can be arranged in a three-dimensional grid, where each voxel comprises a square, cube, and/or hexahedron area in the three-dimensional grid. The plurality of voxels can comprise an x direction, a y direction, and a z direction. The z direction can be the direction of focus of the eye. Each voxel can have a value representing a color of the voxel in the image. For example, a voxel value range can be zero to 65,535 with 65,535 representing complete white and zero representing complete black. In another example, the value range can be zero to 255, zero to 4,095, etc. In some embodiments, voxel values can have a first range (e.g., zero to 65,535) used during processing using method 200, and the voxel values can be converted to a second range (e.g., zero to 255) for display on a display device. In other embodiments, other value ranges can be used. In some embodiments, the image can be comprised of a plurality of voxels in a two-dimensional plane. In some embodiments, a pixel of the image can be identified instead of the voxel.

In some embodiments, the voxel of the image is identified randomly. For example, each voxel can be evenly weighted and a voxel can be chosen completely randomly. In another example, a certain number of voxels can be chosen randomly. In some embodiments, a voxel can be chosen only once. In other embodiments, the voxel is identified using a method. For example, each voxel can be chosen exactly once. In some embodiments, any variation can be used to identify a voxel.

In an operation 215, a neighboring voxel is selected. In some embodiments, a neighboring voxel in the same z plane can be selected. In some instances, the neighboring voxel corresponds to tissue at the same or similar depth. For example, a voxel in the 3×3 neighborhood area around the identified voxel can be selected. In some embodiments, the identified voxel can be included as a neighboring voxel (e.g., a voxel from a total of 9 voxels can be selected). In alternative embodiments, the neighboring voxel can be selected from a three-dimensional neighborhood. The neighboring voxel can be selected randomly. In some embodiments, the selection of the neighboring voxel can be completely random. In other embodiments, the random selection can include a weighted average. For example, the neighboring voxels whose centers are closest to the identified voxel (e.g., the neighboring voxels in the x direction and the y direction in a 3×3 voxel area) can have a higher probability of being selected than neighboring voxels whose centers are further away from the identified voxel (e.g., the neighboring voxels that are diagonal to the identified voxel). In embodiments in which the identified voxel can be selected as a neighboring voxel, the identified voxel can have the highest probability of being selected. In some embodiments, a two-dimensional Gaussian distribution can be used to determine the probability of selecting a neighboring voxel. Part (1) of FIG. 3 illustrates one example of using a two-dimensional Gaussian distribution to select a neighboring voxel.

In alternative embodiments, other probability distributions can be used. In some embodiments, each neighboring voxel location is selected a certain number of times. For example, each neighboring voxel location can be selected once, twice, etc. In another example, each voxel whose center is the closest to the identified voxel is chosen twice and each voxel whose center is furthest from the identified voxel is chosen once. In other embodiments, different methods can be used to select a neighboring voxel. Further, in other embodiments, a different sized region can be used from which to select a neighboring voxel (e.g., a 4×4 area, a 5×5 area, a 7×7 area, voxels with a center that is within a threshold distance, etc.).

In an operation 220, a deviation can be added to the selected voxel's value. In one example, the deviation can range from −6 to 6. In other embodiments, other deviation ranges can be used (e.g., −1 to 1, −2 to 2, −3 to 3, −4 to 4, −5 to 5, −6 to 6, −7 to 7, −8 to 8, −9 to 9, −10 to 10, etc.). In some embodiments, the deviation range can be three standard deviations of the voxel values of the image. In some embodiments, only whole numbers are used. In other embodiments, fractional or decimal numbers can be used. The deviation to be added to the selected voxel's value can be chosen at random. In some embodiments, the deviation can be chosen completely randomly. In other embodiments, the deviations can be weighted according to a probability. For example, the deviation value can be chosen based on a random Gaussian distribution. Such an example is illustrated in part (2) of FIG. 3.

In alternative embodiments, a method can be used to choose the deviation to be added to the selected voxel's value. For example, the deviation to be added can be sequentially chosen. In such an example, for the first selected voxel's value, −6 can be added; for the second selected voxel's value, −5 can be added; for the third selected voxel's value, −4 can be added, etc. In other embodiments, other methods can be used to choose a deviation to be added to the voxel's value.

As shown in FIG. 2, for each identified voxel, operation 215 and operation 220 can be repeated a number of times T1. T1 can be a first threshold number of times. In the example illustrated in part (3) of FIG. 3, T1 can be 15. In other embodiments, operation 215 and operation 220 can be repeated a different number of times, e.g., about 2-about 100 times or any amount in between these two values, e.g., 2, 3, 4, 5, 6, 7, 8, 9, 10, 11, 12, 13, 14, 15, 16, 17, 18, 19, 20, 30, 40, 50, 60, 70, 80, 90, or 100 times. Improvements in the virtually averaged OCT image output by method 200 compared to the image received in operation 205 can diminish with greater values of T1. In some instances, the improvements can be minimal after performing operation 215 and operation 220 about 20 times (i.e., setting T1=20). In some instances, performing operation 215 and operation 220 about 15 times can be an optimal compromise between processing time and improving the OCT image.

In an operation 225, the modified voxel values can be averaged. The values determined in operation 220 for an identified voxel (e.g., the loop defined by decision node N>T1) can be averaged together. An arithmetic average can be used. For example, if operation 215 and operation 220 are repeated about fifteen times for an identified voxel, the fifteen values determined in operation 220 for the identified voxel can be averaged. The average voxel value can be stored, for example in memory 110. The average voxel value can be stored in a virtually averaged OCT image file in which the average voxel value can have a same location as the identified voxel. That is, in some embodiments, the virtually averaged OCT image file can be a version of the original OCT image in which each voxel is an average of the surrounding voxels (as described above).

As shown in FIG. 2, in some embodiments, a new voxel can be identified repeatedly, for example a number of times T2. T2 can be a second threshold number of times to repeat operation 210, operation 215, operation 220, and operation 225. For example, T2 can be the number of voxels in the z plane. In an illustrative embodiment, M can be initialized to be zero at or near the beginning of method 200. In alternative embodiments, different criterion can be used in place of decision node M>T2. For example, a new voxel can be identified until each voxel has been chosen about 1 to about 100 times, or any value in between these two amounts, such as about 2, about 9, about 15, about 20, about 40, or about 100 times, etc. In such embodiments, the multiple averages of the modified voxel values determined in operation 225 can themselves be averaged for each respective voxel location. In some embodiments, operation 215 and operation 220 can be repeated T1 times for each voxel in the received image.

In some embodiments, method 200 is performed once. In some embodiments, method 200 can be repeated for about 2 up to about 100 times, or any value in between these two amounts. For example, the virtually averaged OCT image created by a previously performed method 200 can be the image received in operation 205. Method 200 can be repeated about 1, 2, 3, 4, 5, 6, 7, 8, 9, 10, 11, 12, 13, 14, 15, 16, 17, 18, 19, 20, 30, 40, 50, 60, 70, 80, 90, or 100 times, etc. Improvements in the virtually averaged OCT image output by method 200 compared to the image received in operation 205 can diminish after each time method 200 is performed.

The virtually averaged (non-frame averaged) OCT image can have characteristics such as clarity, sharpness, distinction, etc. that are comparable to an image output by an OCT device using frame averaging. Similarly, if the virtually averaged OCT image and an image output by a frame averaging OCT device are normalized and compared, the images can have similar signal to noise ratios and contrast to noise ratios. Further still, the virtually averaged OCT image and an image output by a frame averaging OCT device can have similar sectoral macular total retinal and circumpapillary retinal nerve fiber layer thickness.

If a virtually averaged OCT image is compared to the original OCT image, the virtually averaged OCT image can have a more distinctive visible nasal side retinal nerve fiber layer. That is, the virtually averaged OCT image can have a distance between the end of the visible nasal side retinal nerve fiber layer and the foveola that is less than that of the original OCT image.

In an illustrative embodiment, any of the operations described herein can be implemented at least in part as computer-readable instructions stored on a computer-readable memory. Upon execution of the computer-readable instructions by a processor, the computer-readable instructions can cause a node to perform the operations.

The subject matter described herein sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

D. Computer Apparatus and Processing

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions.

The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

E. Definitions

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about," "approximate," or "around" will mean up to plus or minus 10% of the particular term.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for virtual averaging of optical coherence tomography (OCT) images comprising:
   (a) receiving an image;
   (b) identifying a first voxel of the image;
   (c) selecting, based on a two-dimensional Gaussian distribution, a plurality of local voxels of the image from among a plurality of neighboring voxels, wherein each voxel of the plurality of neighboring voxels is within a defined region of the first voxel;
   (d) determining a plurality of modified voxel values of the image corresponding to the first voxel by adding a random deviation value to each of the selected plurality of local voxels to determine a corresponding one of the plurality of modified voxel values; and
   (e) determining a virtually averaged voxel value by averaging the plurality of modified voxel values,
   thereby producing a virtually averaged image.

2. The method of claim 1, wherein step (d) comprises selecting the random deviation value for each of the selected plurality of local voxels based on a random Gaussian distribution.

3. The method of claim 1, wherein the image used in step (a) is an OCT image in which frame averaging was not used.

4. The method of claim 1, wherein the image used in step (a) is an OCT image in which frame averaging was used.

5. The method of claim 1, wherein the virtually averaged image, when compared to an original OCT image used in the method, has a more distinctive visible nasal side retinal nerve fiber layer.

6. The method of claim 1, wherein the image comprises a plurality of voxels comprising values indicating an appearance of the image, and wherein the plurality of voxels comprises the first voxel and the plurality of local voxels.

7. The method of claim 6, wherein the plurality of voxels comprise two dimensions.

8. The method of claim 6, wherein the plurality of voxels comprise three dimensions.

9. The method of claim 1, wherein the plurality of local voxels are in a two dimensional plane.

10. The method of claim 1, wherein the method further comprises:
   (f) identifying a next voxel of the image;
   (g) selecting a second plurality of local voxels of the image, wherein each voxel of the second plurality of local voxels is within a defined region of the next voxel;
   (h) determining a second plurality of modified voxel values of the image; and
   (i) determining a second virtually averaged voxel value by averaging the second plurality of modified voxel values.

11. The method of claim 1, wherein the virtually averaged image includes a voxel having the virtually averaged voxel value at the same location as that of the first voxel in the image used in step (a).

12. The method of claim 1, wherein step (c) comprises determining a probability of selecting each voxel of the plurality of neighboring voxels, using the two-dimensional Gaussian distribution.

13. The method of claim 1, wherein the two-dimensional Gaussian distribution is a random distribution.

14. A system for virtually averaging optical coherence tomography (OCT) images comprising one or more data processors and one or more storage devices storing instructions that, when executed by the one or more data processors, cause the one or more data processors to:
   (a) receive an image;
   (b) identify a first voxel of the image;
   (c) select, based on a two-dimensional Gaussian distribution, a plurality of local voxels of the image from among a plurality of neighboring voxels, wherein each voxel of the plurality of neighboring voxels is within a defined region of the first voxel;
   (d) determine a plurality of modified voxel values of the image corresponding to the first voxel by adding a random deviation value to each of the selected plurality of local voxels to determine a corresponding one of the plurality of modified voxel values; and
   (e) determine a virtually averaged voxel value by averaging the plurality of modified voxel values,
   thereby producing a virtually averaged image.

15. The system of claim 14, wherein the instructions further cause the one or more data processors to, in step (d) above, select the random deviation value for each of the selected plurality of local voxels based on a random Gaussian distribution.

16. The system of claim 14, wherein the image used in step (a) is an OCT image in which frame averaging was not used.

17. The system of claim 14, wherein the virtually averaged image, when compared to an original OCT image used in the method, has a more distinctive visible nasal side retinal nerve fiber layer.

18. The system of claim 14, wherein the virtually averaged image includes a voxel having the virtually averaged voxel value at the same location as that of the first voxel in the image used in step (a).

19. The system of claim 14, wherein the instructions further cause the one or more data processors to, in step (c), determine a probability of selecting each voxel of the plurality of neighboring voxels, using the two-dimensional Gaussian distribution.

20. The system of claim 14, wherein the two-dimensional Gaussian distribution is a random distribution.

* * * * *